(12) United States Patent
Wilkinson et al.

(10) Patent No.: US 9,958,368 B2
(45) Date of Patent: May 1, 2018

(54) RHEOMETER CONTROL SYSTEM

(75) Inventors: John Paul Wilkinson, Gloucester (GB); Ian Pearson, Penrith (GB)

(73) Assignee: Malvern Instruments Limited, Malvern (GB)

( * ) Notice: Subject to any disclaimer, the term of this patent is extended or adjusted under 35 U.S.C. 154(b) by 924 days.

(21) Appl. No.: 13/057,155

(22) PCT Filed: Jul. 31, 2009

(86) PCT No.: PCT/GB2009/050962
§ 371 (c)(1),
(2), (4) Date: May 9, 2012

(87) PCT Pub. No.: WO2010/013066
PCT Pub. Date: Feb. 4, 2010

(65) Prior Publication Data
US 2012/0240665 A1    Sep. 27, 2012

Related U.S. Application Data

(60) Provisional application No. 61/137,670, filed on Aug. 1, 2008.

(51) Int. Cl.
*G01N 11/14*    (2006.01)

(52) U.S. Cl.
CPC ................. *G01N 11/142* (2013.01)

(58) Field of Classification Search
USPC ........................................... 73/54.01
See application file for complete search history.

(56) References Cited

U.S. PATENT DOCUMENTS

| | | | | |
|---|---|---|---|---|
| 5,631,409 | A * | 5/1997 | Rajagopal et al. | 73/54.35 |
| 6,065,330 | A * | 5/2000 | Freeman et al. | 73/54.28 |
| 6,499,336 | B1 * | 12/2002 | Raffer | 73/54.28 |
| 7,201,040 | B2 * | 4/2007 | Bateson et al. | 73/54.28 |
| 2002/0138215 | A1* | 9/2002 | Evans et al. | 702/42 |
| 2004/0123650 | A1* | 7/2004 | Kolosov et al. | 73/54.28 |

OTHER PUBLICATIONS

Instrument Engineer's Handbook, Process Measurement and Analysis, Bela Liptak, Fourth Edition, vol. 1, p. 1632, (2003).
Fluids, Colloids, and Soft Materials: An Introduction to Soft Matter Physics, Alberto Fernandez-Nieves, pp. 160-161, Wiley (2016).
A Basic Introduction to Rheology, Section 1, pp. 1-44, Bohlin Instruments (1994).

* cited by examiner

*Primary Examiner* — Peter Macchiarolo
*Assistant Examiner* — Alexander Mercado
(74) *Attorney, Agent, or Firm* — Kristofer E. Elbing

(57) ABSTRACT

A rotary rheometer is disclosed that includes improved control logic. This logic can provide continuously sampled force control logic, compliance control logic, adaptive control logic, anti-windup logic, and/or inertial correction logic.

20 Claims, 4 Drawing Sheets

US 9,958,368 B2

RHEOMETER CONTROL SYSTEM

CROSS-REFERENCE TO RELATED APPLICATION

This application is a US national phase application under 35 USC § 371, and claims priority to PCT patent application number PCT/GB2009/050962 having an International filing date of Jul. 31, 2009, which, in turn, claims priority to U.S. Provisional Patent Application No. 61/137,670, having a filing date of Aug. 1, 2008, both of which are herewith incorporated by reference.

FIELD OF THE INVENTION

This invention relates to rheometers and methods for controlling rheometers.

BACKGROUND OF THE INVENTION

Rheometers are used to study flow and deformation of materials. Rotary rheometers can typically hold a sample between a fixed base plate and a rotating upper plate. In one type of measurement, the gap between the base and rotating upper part is kept constant, and in another, the normal force on the sample is kept constant.

Normal force control has typically been implemented by a simple on-off modulation approach. Upper and lower pass bands are set around the desired normal force loop. A simple step size and update rate are set and the system moves and measures until the force is in the pass band. The control then switches off until the force is seen to move out of the pass bands.

SUMMARY OF THE INVENTION

In one general aspect, the invention features a rheometer for measuring properties of a sample that includes a mobile part having a contact surface for contacting the sample and a fixed part having a contact surface for contacting the sample. The rheometer also includes a vertical actuator for providing relative vertical motion between the mobile part and the fixed part, and a rotary actuator for providing relative rotary motion between the mobile part and the fixed part. A continuously sampled force controller is operative to control a force exerted on the sample by the mobile part and the fixed part through the use of a continuous control signal provided to the vertical actuator. In preferred embodiments the controller is a digital sampled-data controller.

In another general aspect, the invention features a rheometer for measuring properties of a sample that includes a mobile part having a contact surface for contacting the sample and a fixed part having a contact surface for contacting the sample. The rheometer also includes a vertical actuator for providing relative vertical motion between the mobile part and the fixed part, and a rotary actuator for providing relative rotary motion between the mobile part and the fixed part. A vertical controller is operative to control the vertical actuator and includes compliance control logic operative to correct for compliance errors in the rheometer. In preferred embodiments the vertical controller can be operative to correct for compliance errors in a strain gauge.

In a further general aspect, the invention features a rheometer for measuring properties of a sample that includes a mobile part having a contact surface for contacting the sample and a fixed part having a contact surface for contacting the sample. The rheometer also includes a vertical actuator for providing relative vertical motion between the mobile part and the fixed part, and a rotary actuator for providing relative rotary motion between the mobile part and the fixed part. A vertical controller is operative to control the vertical actuator and includes adaptive control logic operative to adapt its control to changes in at least one property of the sample. In preferred embodiments, the controller can be operative to adapt its control based on a modulus of the sample.

In another general aspect, the invention features a rheometer for measuring properties of a sample that includes a mobile part having a contact surface for contacting the sample and a fixed part having a contact surface for contacting the sample. The rheometer also includes a vertical actuator for providing relative vertical motion between the mobile part and the fixed part, and a rotary actuator for providing relative rotary motion between the mobile part and the fixed part. A vertical controller is operative to control the vertical actuator and includes programmable anti-windup logic operative to limit a maximum relative velocity between the mobile part and the fixed part based on a customizable position-velocity profile.

In preferred embodiments, the anti-windup logic can be operative to generate linear profiles. The anti-windup logic can be operative to generate exponential profiles. The anti-windup logic can be operative to combine sub-profiles into larger profiles.

In a further general aspect, the invention features a rheometer for measuring properties of a sample that includes a mobile part having a contact surface for contacting the sample and a fixed part having a contact surface for contacting the sample. The rheometer also includes a vertical actuator for providing relative vertical motion between the mobile part and the fixed part, and a rotary actuator for providing relative rotary motion between the mobile part and the fixed part. A vertical controller is operative to control the vertical actuator and includes inertial compensation logic operative to correct force values for inertial effects during changes in velocity in the mobile part.

Systems according to the invention can be advantageous in that they allow for more precise rheometer control and improved rheometric measurements.

DETAILED DESCRIPTION OF AN ILLUSTRATIVE EMBODIMENT

Figure 1:
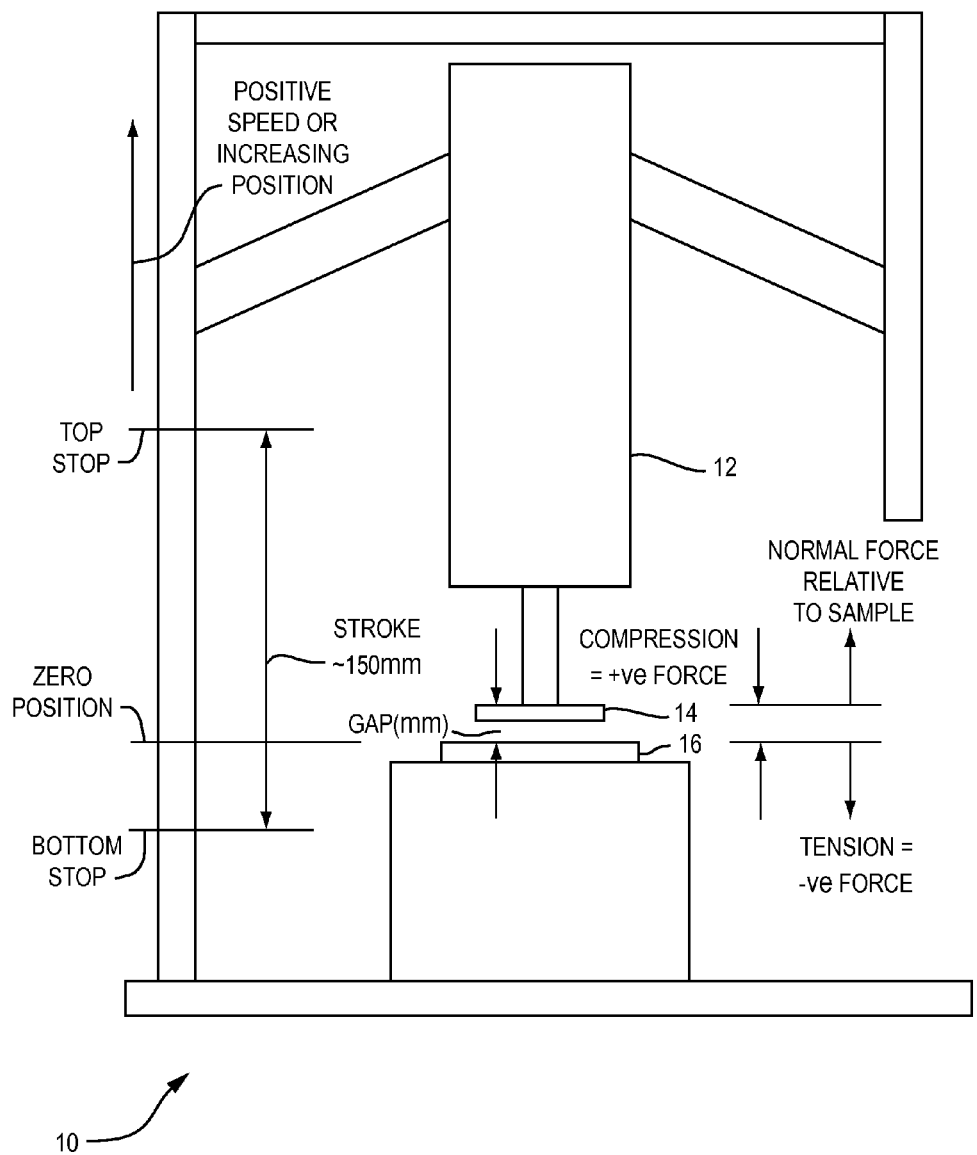
FIG. 1 is a block diagram illustrating the configuration of a rotary a rheometer for a gap and normal force control.

Referring to FIG. 1, a rheometer according to the invention includes a rotary actuator that is operatively connected to a mobile upper part, such as an upper plate. This upper plate and a lower plate are separated by a gap for testing a sample. A vertical actuator is operatively connected to the rotary actuator and can raise or lower it, along with the upper plate to control the gap or the force on the sample in the gap.

Figure 2:
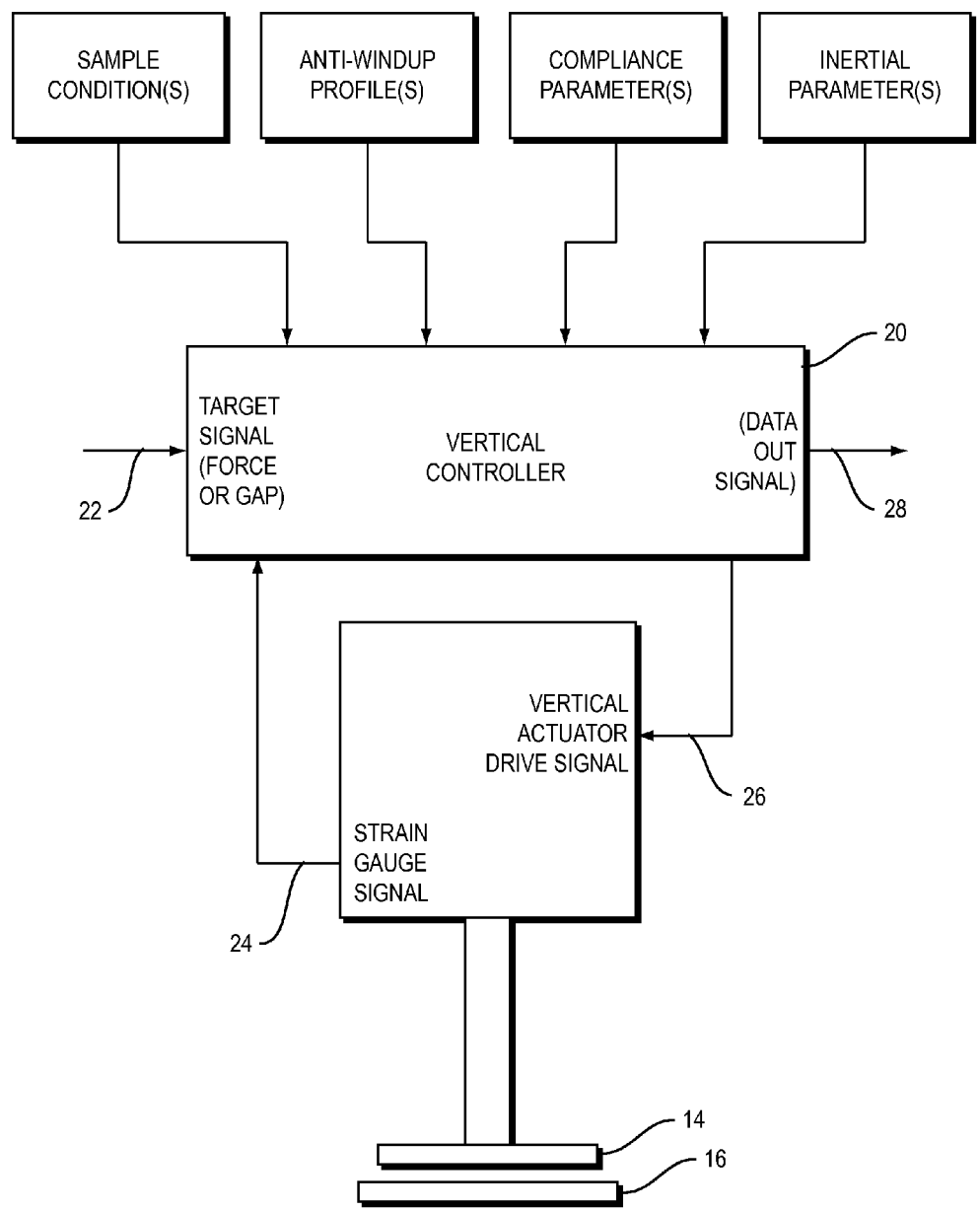
FIG. 2 is a block diagram of a control system for the rheometer of FIG. 1.

Referring to FIG. 2, the vertical actuator of the rheometer is controlled by a vertical controller. This controller is preferably a sampled-data digital controller, although a variety of other types of well-known controllers, such as analog controllers or fuzzy-logic controllers, could also be used.

The vertical controller receives a target gap signal, which can be specified by the user. It also receives a signal from a strain gauge mounted on the vertical actuator and/or the upper part. Based on these signals, the controller generates a vertical actuator drive signal. The vertical controller can also include a data output, which can provide additional data, such as intermediate state data, for display or further calculations.

The vertical controller preferably samples the strain gauge signal on a continuous basis, allowing it to apply a proportional control law to achieve a particular controlled normal force. This represents a significant improvement over prior art on-off control methods. The on-off control of prior art rheometers can have two effects. First, the measured force is typically a saw tooth effect and not particularly constant. The sudden movements can adversely affect the rotational experiment being run and therefore is often switched off during sensitive points in the measurement. The second problem is that unless the two plates are quite close, the user may have to manually move the upper system close using conventional gap control and then wait for the normal force control to "find" the sample which is a fairly undefined length of time. This can be particularly a problem if the sample has limited life time, or if its properties can change significantly over a few seconds. It can also be a problem for short tests like expanding foam where quick approach to the sample is critical if any sensible measurement is to be made.

In implementing its control methodology, the vertical controller can receive sample condition information, an anti-windup profile, compliance parameter information, and/or inertial parameter information. Each of these allows the vertical controller to improve its control methodology.

The sample condition information can be used to adaptively control the rheometer. Normal Force (NF) demand and measured force feed into an adaptive version of the controller, based on a Proportional-Integral-Derivative (PID) loop. The control of normal force manages the fact that the moving geometry may not be in the sample so the force can change rapidly with impact. This could be determined by using a controlled gapping algorithm and detecting a step change in the force then controlling the force, but this can have the problem of not allowing a sensible time for impact as the pre-charging of the control loop plus reacting to the force increase makes it less useful.

A better method is to have the controller running all the time and adapting the controller for changes of effective sample conditions. This is more smooth and continuous and also means it will adapt to changes of sample properties as well. One problem with this is that output demand velocity during the loading process can grow in an uncontrolled way. This needs to be limited by practical working conditions. The solution to this is to feed the maximum velocity into the controller to limit the integrator—a process known as anti-windup.

The rheometer can provide programmable windup profiles. These can limit maximum velocity changes to within predetermined ranges as the plate progresses downward. Illustrative profiles can include linear and exponential profiles. The system can also combine these profiles at the start and end of the overall profile. A user can therefore specify a linear profile to maximum speed and then an exponential profile when the geometry approaches the sample, or vice-versa. Other combinations such as linear/linear or exponential/exponential can also be specified.

The control of the system is essentially a compressive or tensile stress test. The control parameter therefore is the modulus of the material. The modulus of the material can be anything from air (in a no-load situation modulus is zero) to a solid material, hence the need for adaption. With high modulus materials, the compliance of the instrument may come into play. The controller has to accommodate the compliance of the system to ensure that the controlled gap or the reported gap (in the case of force control) is always correct.

If the compliance of the system can be shown to be repeatable it can be corrected out as part of the control methodology. The system compliance may be corrected using a simple gain and offset correction or a higher order correction as appropriate. Typical system compliances are of order a few 10's of microns so unless the gap is significantly less than 1 mm, the error in the measurement is less than 1%.

Figure 3:
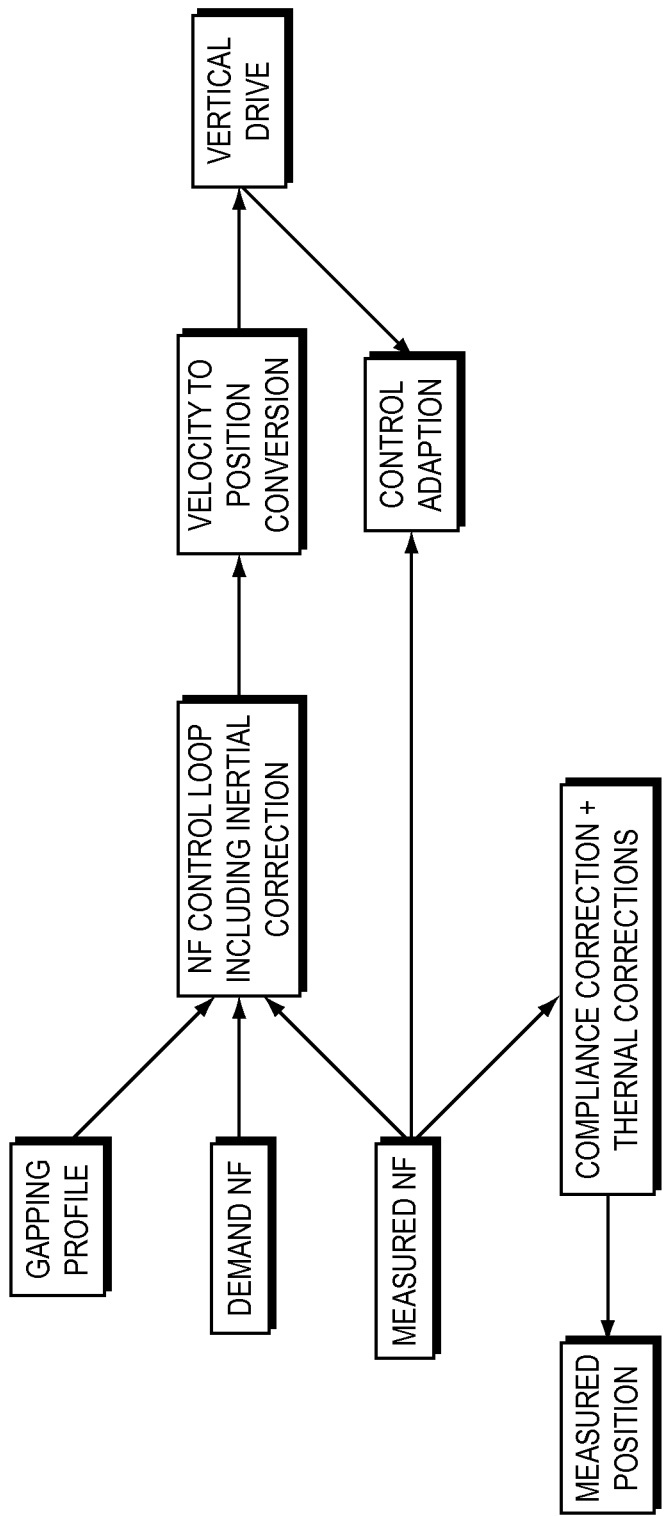
FIG. 3 is a bock diagram illustrating adaptive normal force control with compliance and other corrections for the rheometer of FIGS. 1-2.
Figure 4:
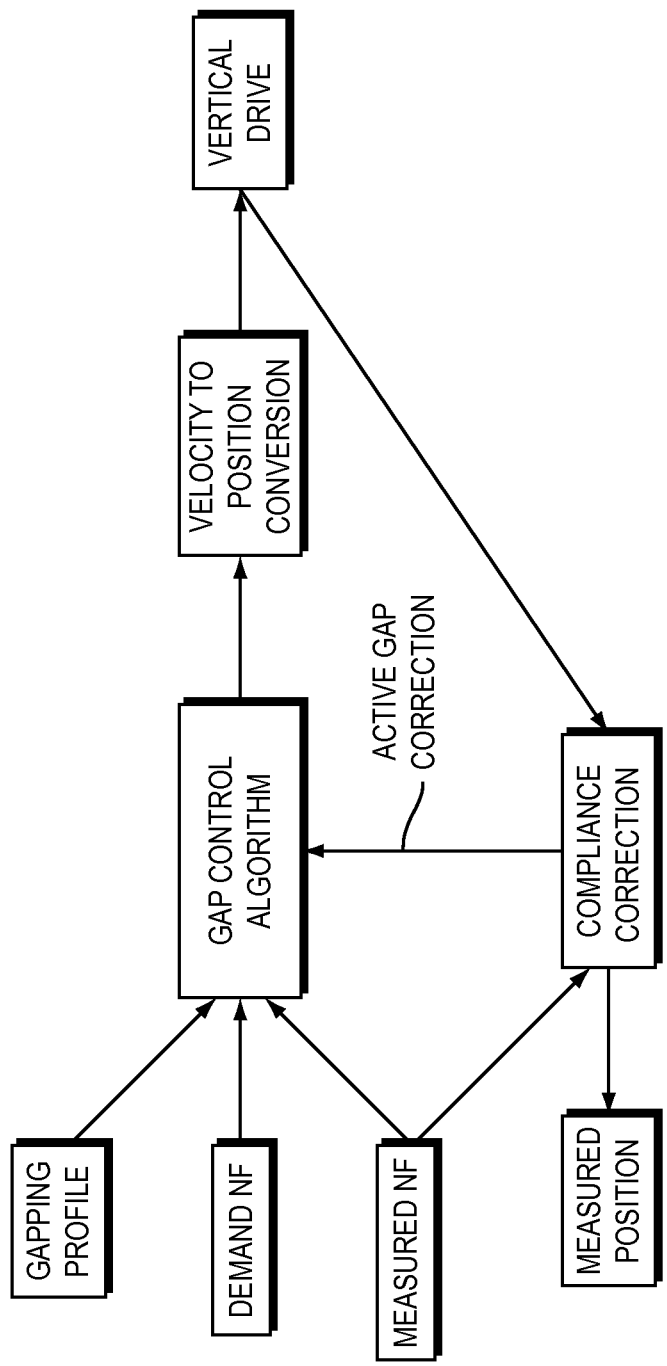
FIG. 4 is a block diagram illustrating gap control with compliance and other corrections for the rheometer of FIGS. 1-2.

Compliance correction is also implemented as an iterative method but can be applied open loop to the reported gap and the loop can be closed to correct for the desired gap if in gap control mode. The compliance correction is open loop in normal force control mode as the normal force is the controlled parameter not the gap. A diagram of the adaptive normal force control method is shown in FIG. 3, and a diagram showing gap control is shown in FIG. 4.

The gapping profile allows a more controlled approach to the sample and also allows the system to stay within the practical working limits of the motor. This has the effect of letting the system approach the sample at controlled velocity thus preventing too much impulse force occurring that could affect future sample performance. The purpose may be for measurement of the compressive or tensile performance of the material or just for sample loading before carrying out some other process.

For a typical sample under compression the force goes up exponentially with decreasing gap. In a controlled compressive stress test, by controlling the normal force, the sample area increases so the stress is decreased logarithmically causing a slowing of the rate of change of gap. In true controlled normal force experiments this means that an on-off control as described earlier will not work well. By using the adaptive feedback control, the variation in rate of change of gap with time is controlled continuously, giving a smooth steady normal force (to within the noise floor constraints of the system) and a more smooth continuous exponentially decaying gap with time.

Another practical application of this is during a stretching test. In this case the material's tensile modulus will be high during the linear region, and then may show plastic failure giving ductile stretching. To model the latter stages properly requires fast control of the changing effect of the material.

The normal force exhibits a force error when the system accelerates, proportional to the mass of the loaded system. The air bearing and torque rotor and the geometry are all part of the weight of the system. When the system accelerates a force is measured on the strain gauge proportional to the mass of the load and the rate of acceleration. This can cause errors in the force control system at low forces, and so it is beneficial to remove it from the control methodology. The system has a characteristic time constant that can be modeled and corrected in the control algorithm.

The compliance correction is applied as a direct correction of the measured gap. The additional correction can be made to the internal demand to correct for the gap error. This is called active compliance correction and is applied to the demand position for the vertical drive actuator. The correction has a loop time constant and this can be corrected out using a lag compensator in the control algorithm if significant oscillation of the control occurs.

In this embodiment, the vertical control system is implemented with special-purpose software written in C++ and running on a general-purpose control processor within the chassis of a rheometric instrument. It is also possible to create an implementation that is based at least in part on specialized custom hardware, or one in which the vertical control system runs from a standard external workstation.

The teachings of this application are useful in connection with the subject matter of two commonly owned provisional applications entitled RHEOMETER WITH MODULAR ENVIRONMENTAL CONTROL SYSTEM, and EXPERT-SYSTEM-BASED RHEOLOGY, both filed on the same day as this application and herein incorporated by reference.

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A rotary rheometer for measuring properties of a sample, comprising:
   a mobile circular plate having a flat circular first side and a second side opposite the first side, wherein the first side includes a first contact surface for contacting the sample,
   a fixed circular plate having a second contact surface for contacting the sample, wherein the contact surface of the fixed circular plate and the contact surface of the mobile circular plate are separated vertically by a gap,
   a vertical actuator operatively connected to the second side of the mobile circular plate for providing relative vertical motion between the mobile circular plate and the fixed circular plate,
   a rotary actuator operatively connected to the second side of the mobile circular plate for providing relative rotary motion between the mobile circular plate and the fixed circular plate, and
   a continuously sampling force controller responsive to a vertical force signal and operative to continuously control a vertical force exerted on the sample by the mobile circular plate and the fixed circular plate based on the vertical force signal during operation of the rotary actuator while a rotational experiment is being run, through the use of a continuous feedback control signal provided to the vertical actuator.

2. The apparatus of claim 1 wherein the continuously sampling force controller is continuously responsive to a target gap signal and to signals from the vertical and rotary actuators to generate the continuous control signal provided to the vertical actuator.

3. The apparatus of claim 1 wherein the continuously sampling force controller implements a proportional control law.

4. The apparatus of claim 1 wherein the continuously sampling force controller continuously receives samples from a strain gauge.

5. A rotary rheometer for measuring properties of a sample, comprising:
   a mobile circular plate having a flat circular first side and a second side opposite the first side, wherein the first side includes a first contact surface for contacting the sample,
   a fixed circular plate having a second contact surface for contacting the sample, wherein the contact surface of the fixed circular plate and the contact surface of the mobile circular plate are separated vertically by a gap,
   a vertical actuator operatively connected to the second side of the mobile circular plate for providing relative vertical motion between the mobile circular plate and the fixed circular plate,
   a rotary actuator operatively connected to the second side of the mobile circular plate for providing relative rotary motion between the mobile circular plate and the fixed circular plate, and
   a vertical controller responsive to a vertical force signal and operative to control the vertical actuator and including compliance control logic operative to correct for compliance errors in the rheometer, wherein the vertical controller is a continuously sampled force controller operative to continuously control a vertical force exerted on the sample by the mobile circular plate and the fixed circular plate based on the vertical force signal through the use of a continuous feedback control signal provided to the vertical actuator.

6. The apparatus of claim 5 wherein the vertical controller is operative to correct for compliance errors in a strain gauge.

7. The apparatus of claim 5 wherein the continuously sampling force controller is continuously responsive to a target gap signal and to signals from the vertical and rotary actuators to generate the continuous control signal provided to the vertical actuator.

8. A rotary rheometer for measuring properties of a sample, comprising:
   a mobile circular plate having a flat circular first side and a second side opposite the first side, wherein the first side includes a first contact surface for contacting the sample,
   a fixed circular plate having a second contact surface for contacting the sample, wherein the contact surface of the fixed circular plate and the contact surface of the mobile circular plate are separated vertically by a gap,
   a vertical actuator operatively connected to the second side of the mobile circular plate for providing relative vertical motion between the mobile circular plate and the fixed circular plate,
   a rotary actuator operatively connected to the second side of the mobile circular plate for providing relative rotary motion between the mobile circular plate and the fixed circular plate, and
   a vertical controller responsive to a vertical force signal and operative to continuously control the vertical actuator and including adaptive control logic operative to adapt its control to changes in at least one property of the sample, wherein the vertical controller is a continuously sampled force controller operative to control a vertical force exerted on the sample by the mobile circular plate and the fixed circular plate based on the vertical force signal through the use of a continuous feedback control signal provided to the vertical actuator.

9. The apparatus of claim 8 wherein the controller is operative to adapt its control based on a modulus of the sample.

10. The apparatus of claim 8 wherein the continuously sampling force controller is continuously responsive to a target gap signal and to signals from the vertical and rotary actuators to generate the continuous control signal provided to the vertical actuator.

11. A rotary rheometer for measuring properties of a sample, comprising:
- a mobile circular plate having a flat circular first side and a second side opposite the first side, wherein the first side includes a first contact surface for contacting the sample,
- a fixed circular plate having a second contact surface for contacting the sample, wherein the contact surface of the fixed circular plate and the contact surface of the mobile circular plate are separated vertically by a gap,
- a vertical actuator operatively connected to the second side of the mobile circular plate for providing relative vertical motion between the mobile circular plate and the fixed circular plate,
- a rotary actuator operatively connected to the second side of the mobile circular plate for providing relative rotary motion between the mobile circular plate and the fixed circular plate, and
- a vertical controller responsive to a vertical force signal and operative to continuously control the vertical actuator and including programmable anti-windup logic operative to limit a maximum relative velocity changes between the mobile circular plate and the fixed circular plate, wherein the vertical controller is a continuously sampled force controller operative to control a vertical force exerted on the sample by the mobile circular plate and the fixed circular plate based on the vertical force signal through the use of a continuous feedback control signal provided to the vertical actuator.

12. The apparatus of claim 11 wherein the anti-windup logic is operative to linearly change the maximum velocity change limit as the mobile circular plate progresses downward.

13. The apparatus of claim 11 wherein the anti-windup logic is operative to exponentially change the maximum velocity change limit as the mobile circular plate progresses downward.

14. The apparatus of claim 11, wherein the anti-windup logic is operative to linearly change the maximum velocity change limit and then exponentially change the maximum velocity change limit as the mobile circular plate progresses downward.

15. The apparatus of claim 11 herein the continuously sampling force controller is continuously responsive to a target gap signal and to signals from the vertical and rotary actuators to generate the continuous control signal provided to the vertical actuator.

16. A rotary rheometer for measuring properties of a sample, comprising:
- a mobile circular plate having a flat circular first side and a second side opposite the first side, wherein the first side includes a first contact surface for contacting the sample,
- a fixed circular plate having a second contact surface for contacting the sample, wherein the contact surface of the fixed circular plate and the contact surface of the mobile circular plate are separated vertically by a gap,
- a vertical actuator operatively connected to the second side of the mobile circular plate for providing relative vertical motion between the mobile circular plate and the fixed circular plate,
- a rotary actuator operatively connected to the second side of the mobile circular plate for providing relative rotary motion between the mobile circular plate and the fixed circular plate, and
- a vertical controller responsive to a vertical force signal and operative to control the vertical actuator and including inertial compensation logic operative to correct force values for inertial effects during changes in velocity in the mobile circular plate, wherein the vertical controller is a continuously sampled force controller operative to continuously control a vertical force exerted on the sample by the mobile circular plate and the fixed circular plate based on the vertical force signal through the use of a continuous feedback control signal provided to the vertical actuator.

17. The apparatus of claim 16 wherein the continuously sampling force controller is continuously responsive to a target gap signal and to signals from the vertical and rotary actuators to generate the continuous control signal provided to the vertical actuator.

18. A rotary rheometric measurement method for measuring the properties of a sample, comprising:
- providing a mobile circular plate having a flat circular first side and a second side opposite the first side, wherein the first side includes a first contact surface for contacting the sample,
- providing a fixed circular plate having a second contact surface for contacting the sample, wherein the contact surface of the fixed circular plate and the contact surface of the mobile circular plate are separated vertically by a gap,
- providing a vertical actuator operatively connected to the second side of the mobile circular plate for providing relative vertical motion between the mobile circular plate and the fixed circular plate,
- providing a rotary actuator operatively connected to the second side of the mobile circular plate for providing relative rotary motion between the mobile circular plate and the fixed circular plate,
- providing a sample between the fixed and mobile circular plates in the gap,
- actuating the rotary actuator to provide relative motion between the mobile circular plate and the fixed circular plate,
- receiving a vertical force signal, and
- continuously controlling a vertical force exerted on the sample by the mobile circular plate and the fixed circular plate based on the vertical force signal during the step of actuating the rotary actuator while a rotational experiment is being run, through the use of a continuous feedback control signal provided to the vertical actuator.

19. The method of claim 18 wherein the step of continuously controlling is responsive to a target gap signal.

20. The method of claim 18 wherein the step of continuously controlling is responsive to a normal force signal.

* * * * *